United States Patent [19]

Matsuo et al.

[11] Patent Number: 4,489,727

[45] Date of Patent: Dec. 25, 1984

[54] DEVICE FOR DIAGNOSING BODY CAVITY INTERIOR WITH SUPERSONIC WAVES

[75] Inventors: Kazumasa Matsuo, Tama; Akio Nakada, Hachioji, both of Japan

[73] Assignee: Olympus Optical Co., Ltd., Tokyo, Japan

[21] Appl. No.: 358,583

[22] Filed: Mar. 16, 1982

[30] Foreign Application Priority Data

Mar. 22, 1981 [JP] Japan .................... 56-40813
Mar. 22, 1981 [JP] Japan .................... 56-40814
Mar. 22, 1981 [JP] Japan .................... 56-40815
Mar. 22, 1981 [JP] Japan .................... 56-40816
Mar. 22, 1981 [JP] Japan .................... 56-39286

[51] Int. Cl.³ ............................................ A61B 10/00
[52] U.S. Cl. .................................. 128/660; 128/6
[58] Field of Search .................. 128/660, 663, 4, 6

[56] References Cited

U.S. PATENT DOCUMENTS 4,176,661 12/1979 Schubert et al. .................. 128/6
4,349,032 9/1982 Koyata ............................ 128/660
4,401,123 8/1983 Baba ............................... 128/660

FOREIGN PATENT DOCUMENTS 55-94230 7/1980 Japan ............................ 128/4
55-94231 7/1980 Japan ............................ 128/4
55-96130 7/1980 Japan ............................ 128/4
55-96132 7/1980 Japan ............................ 128/4

OTHER PUBLICATIONS

Baba K., "UTS Wave Diagnosis Device With Endoscope", Europ. Pat. Appln. EP 066185, published Dec. 1982.

Primary Examiner—Kyle L. Howell
Assistant Examiner—Francis J. Jaworski
Attorney, Agent, or Firm—Armstrong, Nikaido, Marmelstein & Kubovcik

[57] ABSTRACT

There is disclosed a device for diagnosing a body cavity interior with supersonic waves which is to be inserted into a body cavity wherein the tip of a supersonic wave probe is in direct contact with an internal organ within the body cavity. An endoscope and supersonic probe are arranged to make it possible to diagnose the internal organ with supersonic waves while the supersonic wave probe tip is being observed.

4 Claims, 12 Drawing Figures

DEVICE FOR DIAGNOSING BODY CAVITY INTERIOR WITH SUPERSONIC WAVES

BACKGROUND OF THE INVENTION

In prior art devices for supersonic wave diagnosing internal organs within a body cavity by combining a supersonic wave probe means transmitting and receiving supersonic waves and an endoscope for observing the interior of the body cavity with each other, the field of vision of the above mentioned endoscope is blocked by the supersonic wave probe means, the position in which the tip of the supersonic wave probe transmitting and receiving supersonic waves is to be contacted with an internal organ can not be sighted, the tip of the above mentioned supersonic wave probe can not be observed and, as a result, in what position the tip of the supersonic wave probe is in contact with the internal organ can not be confirmed. Therefore, the body cavity interior supersonic wave diagnosing device of the present invention makes it possible to sight with an endoscope the tip of a supersonic wave probe having a window for transmitting and receiving supersonic waves.

SUMMARY OF THE INVENTION

This invention relates to an improved device for diagnosing a body cavity interior with supersonic waves wherein an endoscope is incorporated in a supersonic wave probe body so that the tip of the supersonic wave probe can be contacted with an internal organ to be diagnosed while its window for transmitting and receiving supersonic waves is being observed.

A means of obtaining information on an object by utilizing supersonic waves has recently come to be extensively used even in the medical field. For example, when supersonic wave pulses are projected into a body from the body surface, the above mentioned projected supersonic waves will be propagated and will be reflected by a discontinuous boundary surface of an acoustic impedance represented by the product of the density of the medium and the velocity of the sound. The above mentioned reflected supersonic wave pulses will be received and such acoustic information as the reflecting intensity will be utilized for the diagnosis.

As compared with an X-ray device, such supersonic wave diagnosing device has advantages in that information on a biotic soft structure can be easily obtained without using a molding agent, biotic structure is not destroyed by radioactive rays, and the device is easier to handle and is less dangerous. Further, recently the technique of supersonic waves has progressed and the obtained information has been improved in the quality and quantity so much that the supersonic wave diagnosing device is being popularized as a clinical diagnosing device.

As opposed to the above mentioned diagnosis wherein supersonic wave pulses are transmitted and received from the surface of a body, the body cavity interior supersonic wave diagnosing method wherein supersonic wave pulses are transmitted and received from a position near a biotic internal organ within a body cavity has advantages in that it is possible to use a high frequency and obtain information of high precision. Such diagnosis is not influenced by a hypodermic fat layer or the like interposed between objects, and therefore will be used more in the future. Such a supersonic wave diagnosing device to be inserted into a body cavity is generally and conveniently used by incorporating an endoscope as an optical observing means.

In the prior arts of such body cavity interior supersonic wave diagnosing devices wherein a supersonic wave probe inserted into a body cavity for transmitting and receiving supersonic waves to and from an internal organ and an endoscope are combined with each other, there are disclosed a "Probe for Inspecting a Body Cavity Interior" mentioned in the Gazette of Japanese Patent Laid Open No. 94230/1980, a "Body Cavity Interior Inspecting probe" mentioned in the Gazette of Japanese Patent Laid Open No. 94231/1980, a "Supersonic Wave Probe" mentioned in the Gazette of Japanese Patent Laid Open No. 96130/1980 and an "Endoscope" mentioned in the Gazette of Japanese Patent Laid Open No. 96132/1980. However, in each of the above mentioned prior art devices the supersonic wave probe tip for transmitting and receiving supersonic waves can not be seen with the combined endoscope. Therefore, the accurate positioning of the tip of the supersonic wave probe in contact with an internal organ, and the orientation of the supersonic wave probe tip in contact with the internal organ can not be observed.

An object of the present invention is to provide a device for diagnosing a body cavity interior with supersonic waves wherein the field of vision of an endoscope is not obstructed by the inserted supersonic wave probe tip and curved part, the supersonic wave probe tip can be accurately and safely inserted and guided while the body cavity interior is being observed with the endoscope, and the supersonic wave probe tip can be positively positioned so as to be in close contact with an internal organ while both the supersonic wave probe tip and internal organ are observed.

Another object of the present invention is to provide a body cavity interior supersonic wave diagnosing device wherein the curved direction of the curved part is set in the direction of the field of vision of an endoscope so that both a window for transmitting and receiving supersonic waves at the tip of a supersonic wave probe and an internal organ can be positively observed and, as a result, the above mentioned window for transmitting and receiving supersonic waves can be accurately positioned.

Further, another object of the present invention is to provide a body cavity interior supersonic wave diagnosing device wherein the direction of the field of vision of an endoscope and the direction of the window for transmitting and receiving supersonic waves in a supersonic wave probe tip are so arranged as to intersect at right angles with each other so that the orientation of the window for transmitting and receiving supersonic waves in contact with an internal organ can be directly observed.

Another object of the present invention is to provide a body cavity interior supersonic wave diagnosing device wherein, for diagnosing abdomen cavity internal organs, the direction of the field of vision of an endoscope and the curved direction of the curved part are arranged to permit the observation of an internal organ within the abdomen and the contact of the supersonic wave probe tip with the internal organ.

Other objects, features and advantages of the present invention will become apparent enough by the following explanation.

BRIEF DESCRIPTION OF THE DRAWINGS

FIG. 3 is a general schematic view of a device for diagnosing a body cavity interior with supersonic waves.

DETAILED DESCRIPTION OF THE INVENTION

Figure 1:
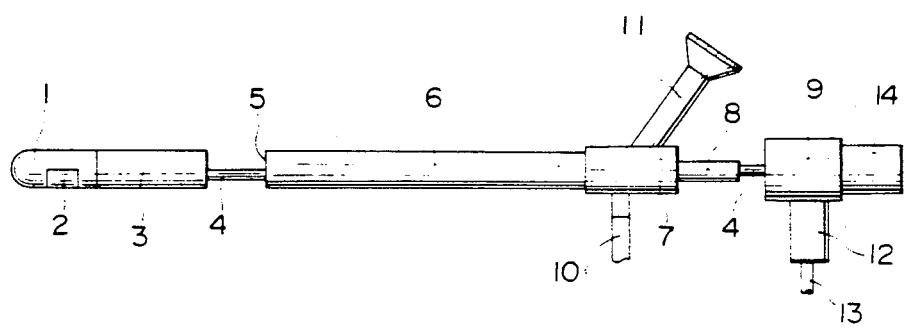
FIG. 1 is an elevation showing a conventional body cavity supersonic wave diagnosing device.

Prior to explaining an embodiment of the present invention, a conventional example of a device for diagnosing a body cavity interior with supersonic waves wherein an endoscope for observing a body cavity interior and a supersonic wave probe for obtaining a supersonic wave signal image are combined with each other shall be explained with reference to FIGS. 1 and 2. In these drawings, the reference numeral 1 indicates a supersonic wave probe tip, a window 2 for transmitting and receiving supersonic waves is formed in the side part of the tip and a small diameter shaft 4 is connected to the rear part of the tip through a curved part 3. Cords for transmitting and receiving supersonic waves and wires (not illustrated) for driving a mirror within the above mentioned supersonic wave probe tip 1 are contained in this shaft. This shaft 4 is passed through a channel in an inserted part 6 in which an endoscope 5 is arranged and is connected at the rear end to a driving part 9 through an endoscope hand part 7 and channel inserting port 8. A light guide cable 10 and an eyepiece part 11 inclined to the axial direction of the inserted part 6 are connected to the above mentioned hand part 7. A holding handle 12 is connected below the driving part 9. A signal cable 13 is inserted through the handle 12. A driving motor 14 is connected to the rear of the driving part 9.

Figure 2:
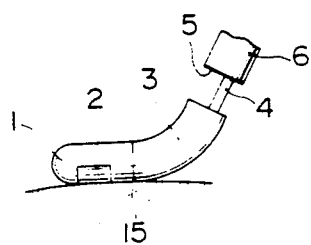
FIG. 2 is an explanatory view of the diagnosing device in FIG. 1 as being used.
Figure 3:
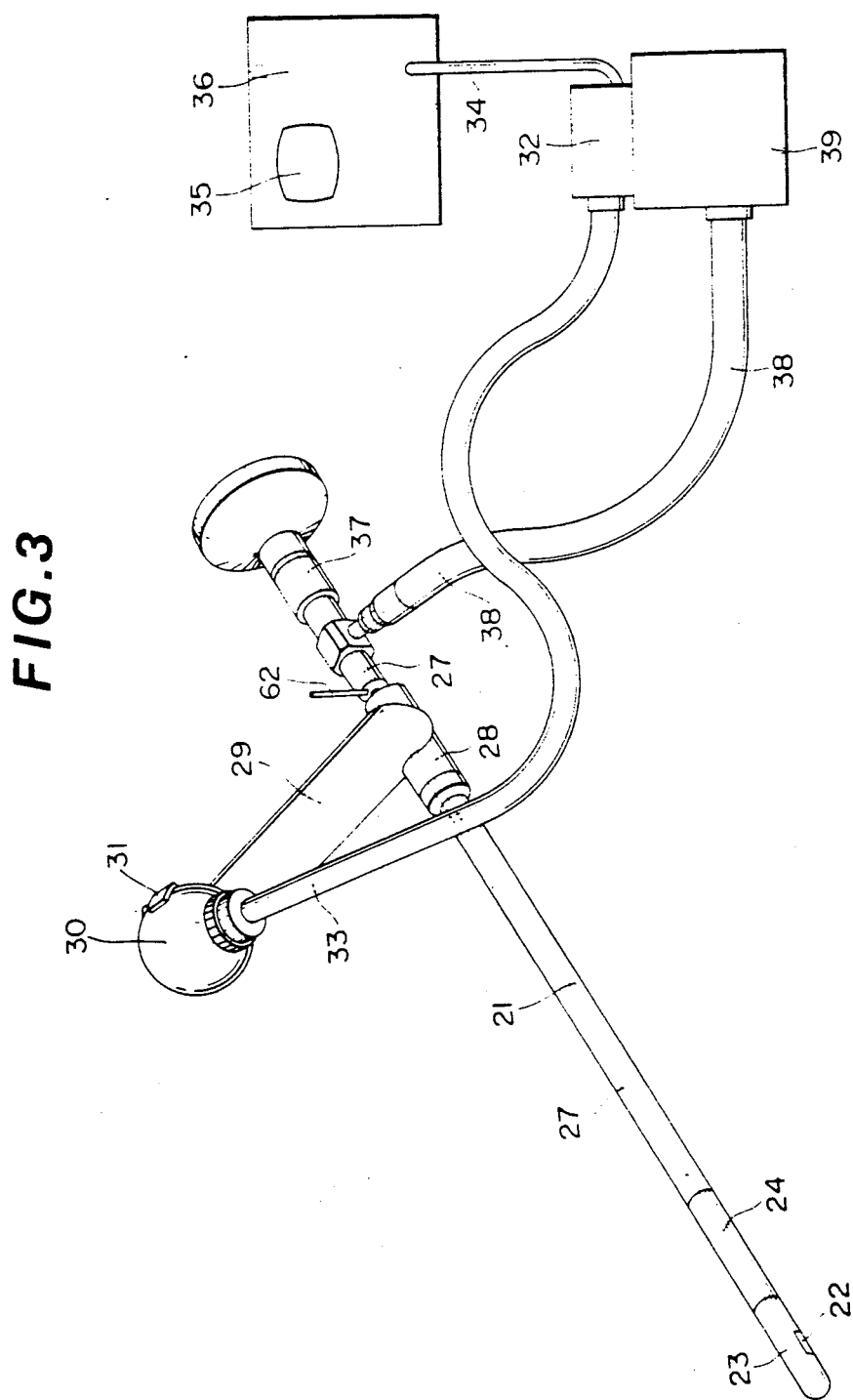
FIG. 3 and others following it show an embodiment of this invention.
Figure 4:
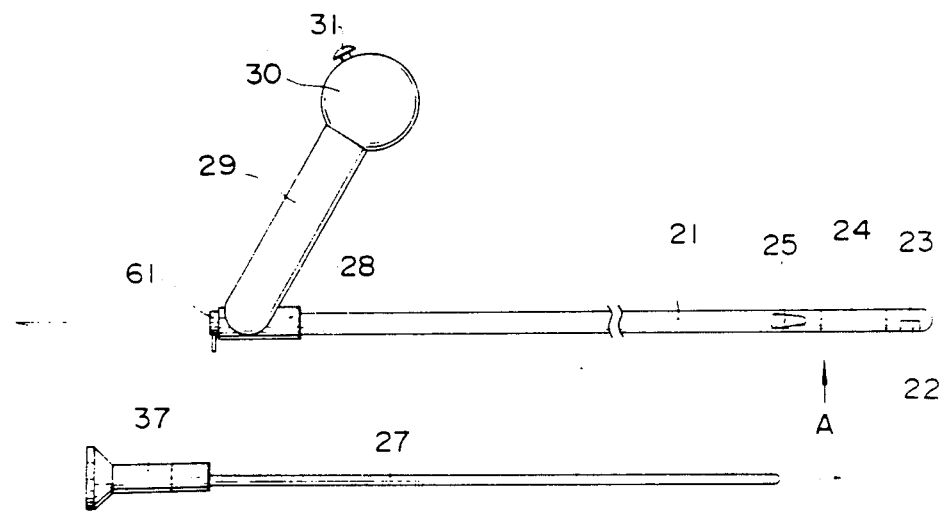
FIG. 4 is an elevation showing an endoscope with an inserted part pulled out.
Figure 5:
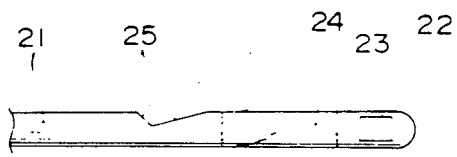
FIG. 5 is a view as seen in the direction indicated by the arrow A in FIG. 4.

In the above described supersonic wave diagnosing device, in order to obtain a supersonic wave image, the inserted part 6 and supersonic wave probe tip 1 are inserted into a body cavity, the supersonic wave probe tip 1 is pressed to be pushed down in contact with a predetermined internal organ 15 caught within the field of vision of the endoscope 5 within the inserted part 6 and the curved part 3 is curved as shown in FIG. 2 so as to bring the window 2 of the supersonic wave probe tip 1 into contact with the internal organ 15.

However, in the above mentioned conventional device, the supersonic wave probe tip 1 and curved part 3 project to be so comparatively far forward of the tip of the endoscope 5 that, when they are inserted into a body cavity and the supersonic probe tip 1 is brought into close contact with the internal organ 15, the field of vision of the endoscope 5 will be blocked, while the inserted part 6 will have to be pressed down to curve the curved part 3 into contact with the organ. This operation is difficult and requires a skilled technique. This is not desirable.

Therefore, the present invention is made to solve the problems of the above mentioned conventional example and prior art.

A body cavity interior supersonic wave diagnosing device embodying the present invention shall be explained in the following with reference to FIGS. 3 to 12. In these drawings, the reference numeral 21 indicates an inserted part, a supersonic wave probe tip 23 having a window 22 for transmitting and receiving supersonic waves on the side surface and a curved part 24 are connected in turn from the front to the tip of this inserted part 21 and these inserted part 21, supersonic wave probe tip 23 and curved part 24 are formed to be of substantially the same diameter. An angled window 25 incised in the direction of the field of vision is formed on the outer periphery of the inserted part 21 in the rear of the above mentioned curved part 24, an endoscope guide tube 26 is arranged from this incised window 25 to the rear end of the inserted part 21 and a perspective endoscope 27 of a fine diameter is telescopically inserted in the guide tube 26. In the illustrated abdomen cavity internal organ diagnosing device, the incised window 25 formed in the inserted part 21 is in the right hand direction as seen from the operator in the normal using state so that the tip of the perspective endoscope 27 may be positioned in this incised window 25 so that the diagonally right front area is within the field of vision of the endoscope. The above mentioned perspective endoscope 27 has a field of vision of substantially 45 degrees or more. Also, the incised window 25 formed in the inserted part 21 has a vision field direction inclination angle of 5 to 25 degrees so that the field of vision of the endoscope 27 may not be blocked by the outer periphery of the inserted part 21.

A hand part body 28 is connected to the rear end of the above mentioned inserted part 21. A grip 29 inclined forward by about 60 degrees with the axial direction is integrally connected to the outer periphery of the upper part of this hand part body in the normal using state so as to be gripped with one hand by the operator so that in particular, even if the inserted part 21 is greatly inclined in being inserted into a body cavity to diagnose a deep internal organ, the grip 29 will not contact the body wall and will not be in the way. The head of the grip 29 has a substantially spherical curved operating part 30 on which a curved operating lever 31 is provided to project so as to be operated with the thumb of the hand gripping the above mentioned grip 29.

A driving means 32 containing a motor for scanning supersonic waves is formed separately from the above mentioned grip 29. This driving means 32 and the grip 29 are connected with each other through a flexible driving cable 33. Further, the driving means 32 is connected to an indicating means 36 provided with a Braun tube 35 through a signal cable 34. A flexible light guide cable 38 is connected in front of an eyepiece part 37 of the above mentioned perspective endoscope 27 so as to be connected to a light source means 39. This light guide cable 38 and the above mentioned driving cable 33 are connected in the same lateral direction respectively with the eyepiece part 37 of the endoscope and the curved operating part 30 of the head of the grip 29 to improve the operability so as not to interfere with the insertion of the inserted part 21 into the body cavity, the operation of contacting the supersonic wave probe tip 23 with a predetermined internal organ and the diagnosing operation with supersonic waves.

Figure 6:
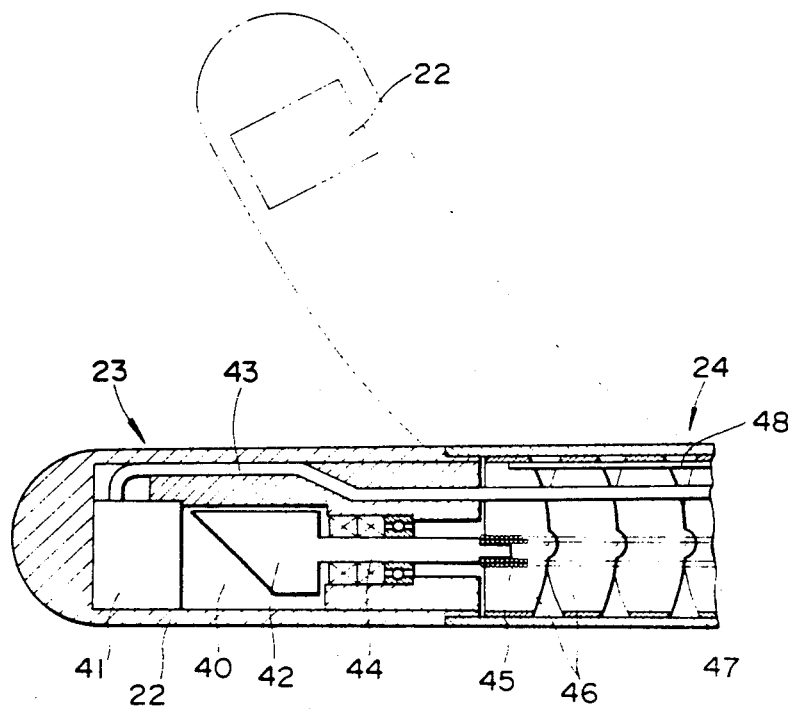
FIG. 6 is a sectioned view showing a supersonic wave probe tip and curved part.

The supersonic wave probe tip 23 and curved part 24 are formed as shown in FIG. 6. That is to say, a medium chamber 40 is formed in the supersonic wave probe tip 23. A supersonic wave oscillator 41 and a mirror 42 are arranged as opposed to each other within this chamber 40. A signal cable 43 inserted through the inserted part 21 from the driving means 32 is connected to this oscillator 41. A shaft 44 is formed on the mirror 42. A flexible driving shaft 45 is connected to this shaft 44. On the other hand, the curved part 24 is formed by pivoting a plurality of articulated members 46 which are coated with a coating of rubber 47. Further, an operating wire 48 inserted through the curved operating part 30 is fixed to the articulated member 46 at the front end.

Figure 12:
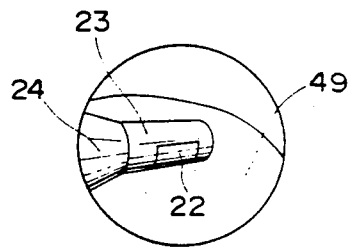
FIG. 12 is an explanatory view showing the field of vision of the endoscope in FIG. 11.

The curved direction of this curved part 24 is set in the direction of the field of vision of the endoscope 27, that is, in the right direction as seen from the operator in the normal using state so that the window 22 for transmitting and receiving supersonic waves may be within the field of vision of the endoscope 27 as shown in FIG. 12. Thus, in the illustrated device for diagnosing internal organs within the abdomen cavity, the direction of the field of vision of the endoscope 27 inserted in the inserted part 21 and the curved direction of the curved part 24 are set to the right hand side as seen from the operator because, in the case of using the device to diagnose an internal organ 49 within an abdomen cavity, in what part of the skin there are many blood vessels and in what position the internal organ is located are naturally known, therefore the inserting position and inserting direction are medically known. Therefore, if the field of vision is to the right in the normal using state and the curved part is curved in the direction of the field of vision, the device will be adapted to such operation and observation as the observation of the internal organ and the close contact of the supersonic wave probe tip 23 within the internal organ. Therefore, it is needless to say that, in the device to be used to diagnose other than internal organs within the abdomen cavity with supersonic waves, the above mentioned direction of the field of vision of the endoscope and curved direction need not be to the right. Further, the supersonic wave transmitting and receiving window 22 provided in the supersonic wave probe tip 23 is arranged in a position intersecting at right angles with the direction of the field of vision of the endoscope, that is, the curved direction.

Figure 7:
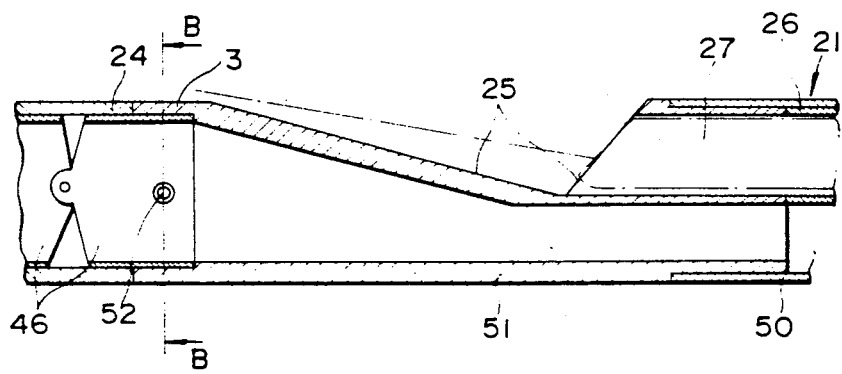
FIG. 7 is a sectioned view showing an incised window in the inserted part and a connecting structure of the curved part and a connecting member.
Figure 8:
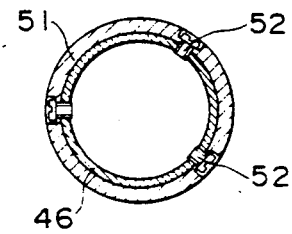
FIG. 8 is a sectioned view on line B—B in FIG. 7.
Figure 9:
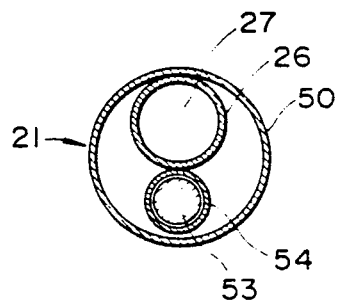
FIG. 9 is a cross-sectioned view of the inserted part.

As shown in FIG. 7, the incised window 25 formed in the inserted part 21 is formed in a connecting member 51 connecting the tip of a jacket tube 50 forming the inserted part 21 and the curved part 24 with each other. This connecting member 51 is fitted and fixed on the side toward jacket tube 50 inside the jacket tube 50, is engaged on the sided toward curved part 24 with the articulated member 46 inside connecting member 51 and fixed thereto with screws 52 screwed in from the outer periphery outside the connecting member 51. By this construction, a wide space can be obtained inside the connecting part of the connecting member 51 containing a driving shaft 53, signal cable 43 and operating wire 48 with the articulated member 46. Further, as shown in FIG. 9, in order to enlarge the incised window 25 formed in the above mentioned inserted part 21, the mirror driving shaft 53 inserted through the jacket tube 50 of the inserted part is arranged on the side opposite the direction of the field of vision of the endoscope 27.

Figure 10:
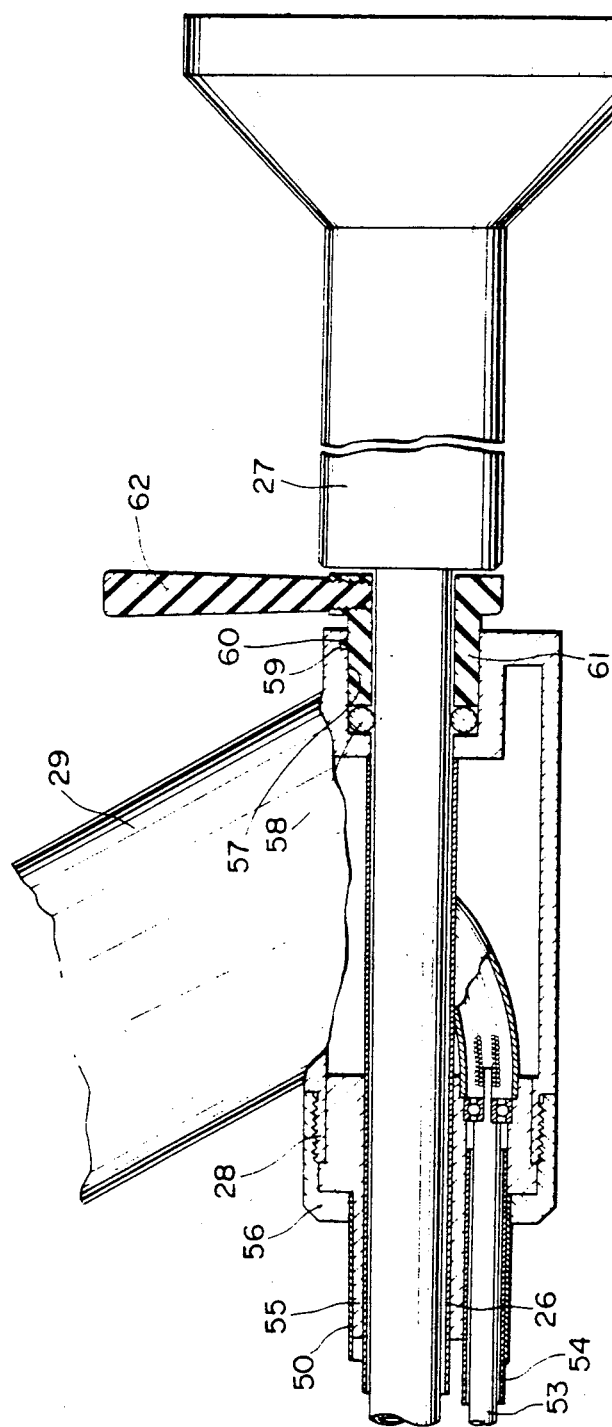
FIG. 10 is a view showing a hand part body with an essential part sectioned.

Further, the connection of the inserted part 21 and hand part body 28 with each other is as shown in FIG. 10. That is to say, a pipe receiver 55 holding and fixing the endoscope guide tube 26, driving shaft tube 54 and inserted part jacket tube 50 is fitted within the hand part body 28, a male screw is formed on the outer periphery of this hand part body 28 and a cap 56 having a female screw is screwed on the male screw from the outer peripheral direction to press and fix the above mentioned pipe receiver 55 to the hand part body 28. On the other hand, a fixing hole 57 communicating with the endoscope guide tube 26 is formed on the rear end of the hand part body 28. An O-ring 58 engaging with the outer periphery of the endoscope 27 is inserted in this fixing hole 57. Further, an O-ring fastening body 61 projecting a pin 60 engaged in a spiral groove 59 provided on the inner periphery within the hole 57 is screwed in the above mentioned fixing hole 57 to press and deform the above mentioned O-ring 58. The endoscope 27 is fastened with this deformed O-ring to be fixed in the removing direction and rotating direction and to be kept airtight. The above mentioned ring fastening body 61 is tubularly formed to insert the endoscope 27 and is provided with a lever 62 to project on the outer periphery of the rear part.

Figure 11:
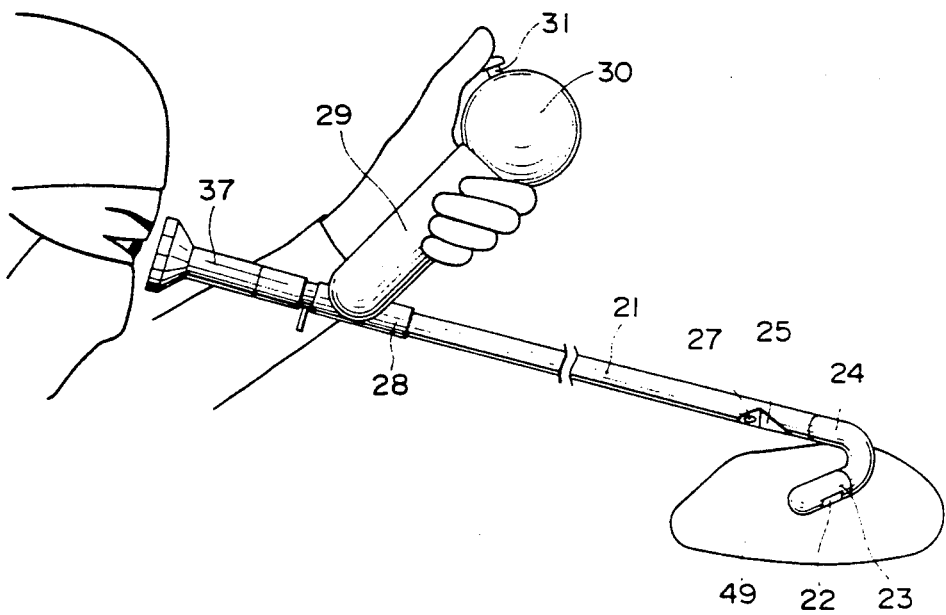
FIG. 11 is an explanatory view showing the device as being used.

In such formation, as shown in FIG. 11, the grip 29 is gripped with one hand by the operator and the inserted part 21 is inserted into a body cavity, for example, an abdomen cavity through a trocar not illustrated with the inside of the thumb applied to the curved operating lever 31 of the substantially spherical curved operating part formed in the head of the grip 29. In such case, the supersonic wave probe tip 23 is guided to an internal organ while, for example, the diagonal front in the right direction of the inserted part 21 is being observed with the perspective endoscope 27 in the rear of the curved part. After the internal organ 49 is confirmed, the curved operating lever 31 is operated with the above mentioned thumb to pull the operating wire 48 to curve the curved part 24 in the direction of the field of vision of the endoscope 27 or to the right hand side as seen from the operator in diagnosing the abdomen cavity interior, thus the supersonic wave probe tip 23 and window 22 for transmitting and receiving supersonic waves are brought into the field of vision and the above mentioned window 22 for transmitting and receiving supersonic waves is brought into close contact with a predetermined part of the internal organ 49 while the internal organ 49, the probe tip 23 and window 22 are all being observed as shown in FIG. 12.

As the endoscope 27 is made to be in the incised window 25 formed in the inserted part 21 side part in the rear of the curved part 24 and is perspective at the tip as mentioned above, the supersonic wave probe tip 23 and curved part 28 can be inserted while the internal organ is being observed without blocking the field of vision and further, as the supersonic wave probe tip 23 can be curved in the direction of the field of vision of the endoscope 27, the operation of close contacting the internal organ 49 can be accomplished while both the internal organ 49 and supersonic wave probe tip 23 are being observed and the internal organ can be accurately and easily diagnosed. Also, the orientation of the window 22 for transmitting and receiving supersonic waves in contact with the internal organ can be confirmed.

By the way, in the present invention, the endoscope 27 is made to be telescopically inserted into the inserted part 21 as in the above mentioned embodiment so that the inserted part 21 and the endoscope 27 may be separable from each other, can be any already made fine diameter endoscope or can be so formed that, in case one fails, only it may be repaired or replaced. On the other hand, the endoscope may be integrally contained in the inserted part so as not to require sterilization of the endoscope inserting tube inserted into the above mentioned inserted part.

It is apparent that different working modes can be formed in a wide range without departing from the spirit and scope of the present invention. Therefore, the present invention is not restricted by the specific working mode except by being limited in the appended claims.

We claim:

1. A combination endoscope and supersonic diagnostic probe for examining an internal organ within a body cavity comprising:
    a part adapted to be inserted into said body cavity, said inserted part including a supersonic wave probe tip positioned at its extremity, a flexible portion adjacent to said tip adjustably curvable in a locus plane of curvature, and a window for a perspective endoscope angularly incised in said inserted part above and adjacent to said flexible portion;
    said supersonic wave probe tip being formed with a window for transmission of supersonic waves in a direction substantially at right angles to said locus plane of curvature and positioned where it may be brought into contact with said organ by manipulation of said flexible portion; and
    said incised viewing window being so positioned that the observing direction of a perspective endoscope telescopically inserted into said inserted part will be along said locus plane of curvature whereby said supersonic wave probe tip may be observed as it is manipulated to bring said supersonic wave transmission window into contact with said organ.

2. A combination endoscope and supersonic probe for examining an organ within a body cavity comprising:
    a part adapted to be inserted within said body cavity including a jacket tube, an articulated flexible member, and a supersonic wave probe tip;
    said articulated flexible member being connected at one end to said jacket tube and at its other end to said probe tip and having connected thereto an operating wire manipulable to bend said articulated flexible member in a locus plane of curvature;
    said supersonic wave probe tip including therewithin means for transmitting supersonic waves and having in its surface a window through which said supersonic waves are transmitted and received and adapted to be positioned against said internal organ by the bending of said articulated member;
    said jacket tube having therewithin a hollow guide tube for receiving a perspective endoscope and having angularly incised in its end adjacent to said articulated flexible member a viewing window angled along said locus plane of curvature in the direction toward which said articulated flexible member bends; and
    a perspective endoscope telescopically positionable in said hollow guide tube so that its field of vision through said viewing window includes said supersonic wave probe tip window as it is positioned against said internal organ by manipulation of said operating wire.

3. A combination endoscope and supersonic probe as claimed in claim 2 wherein said viewing window is incised at an acute angle with respect to said jacket tube.

4. A combination endoscope and supersonic probe as claimed in claim 3 wherein the direction of the supersonic waves transmitted by said supersonic wave probe is at right angles to the direction of the field of vision of said endoscope.

* * * * *